(12) United States Patent
Ernster

(10) Patent No.: US 6,250,315 B1
(45) Date of Patent: Jun. 26, 2001

(54) DEVICE FOR CLEANING NASAL COAGULATOR

(76) Inventor: Joel A. Ernster, 715 N. Cascade Ave., Colorado Springs, CO (US) 80903

( * ) Notice: Subject to any disclaimer, the term of this patent is extended or adjusted under 35 U.S.C. 154(b) by 0 days.

(21) Appl. No.: 09/223,682

(22) Filed: Dec. 30, 1998

(51) Int. Cl.[7] .................................................. B08B 9/00
(52) U.S. Cl. ............................... 134/22.12; 134/166 R; 134/199; 134/201; 134/170
(58) Field of Search ..................... 134/170, 171, 134/166 R, 169 R, 199, 201, 22.1, 22.11, 22.12

(56) References Cited

U.S. PATENT DOCUMENTS

| | | | |
|---|---|---|---|
| 4,015,614 | * | 4/1977 | Jonsson et al. . |
| 4,422,466 | * | 12/1983 | Schafer . |
| 4,784,167 | * | 11/1988 | Thomas et al. . |
| 4,785,836 | * | 11/1988 | Yamamoto . |
| 5,213,117 | * | 5/1993 | Yamamoto . |
| 5,472,004 | * | 12/1995 | Gilliard . |
| 5,863,349 | * | 1/1999 | Laub-Maier et al. . |
| 6,041,797 | * | 3/2000 | Casselman . |

* cited by examiner

Primary Examiner—Frankie L. Stinson
(74) Attorney, Agent, or Firm—Gibson, Dunn & Crutcher LLP

(57) ABSTRACT

A device for cleaning a nasal coagulator or similar instrument. The nasal coagulator is of the type that has a generally cylindrical sidewall defining a bore, in which char or the like accumulates. The device has a generally cylindrical sidewall which defines a chamber, and a flared trumpet-like ending. A prong is located within the chamber, and two slit apertures are foxed in the sidewall to communicate the chamber and the exterior of the device. In use, the coagulator is inserted into the cleaning device so that that the prong loosens any char, and the coagulator is rotated so that the char exits the slit apertures.

16 Claims, 1 Drawing Sheet

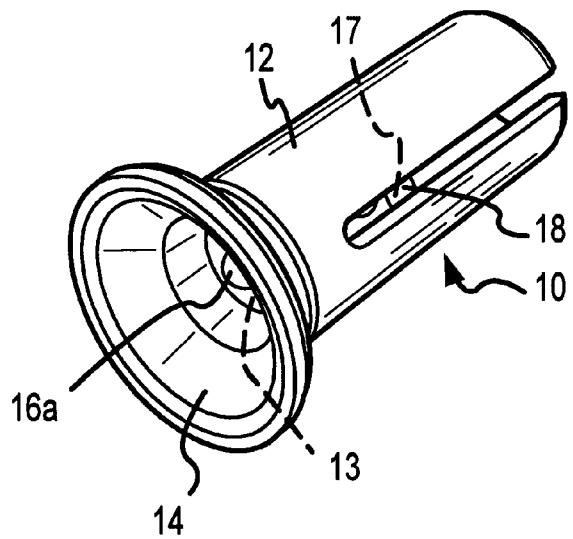
FIG.1
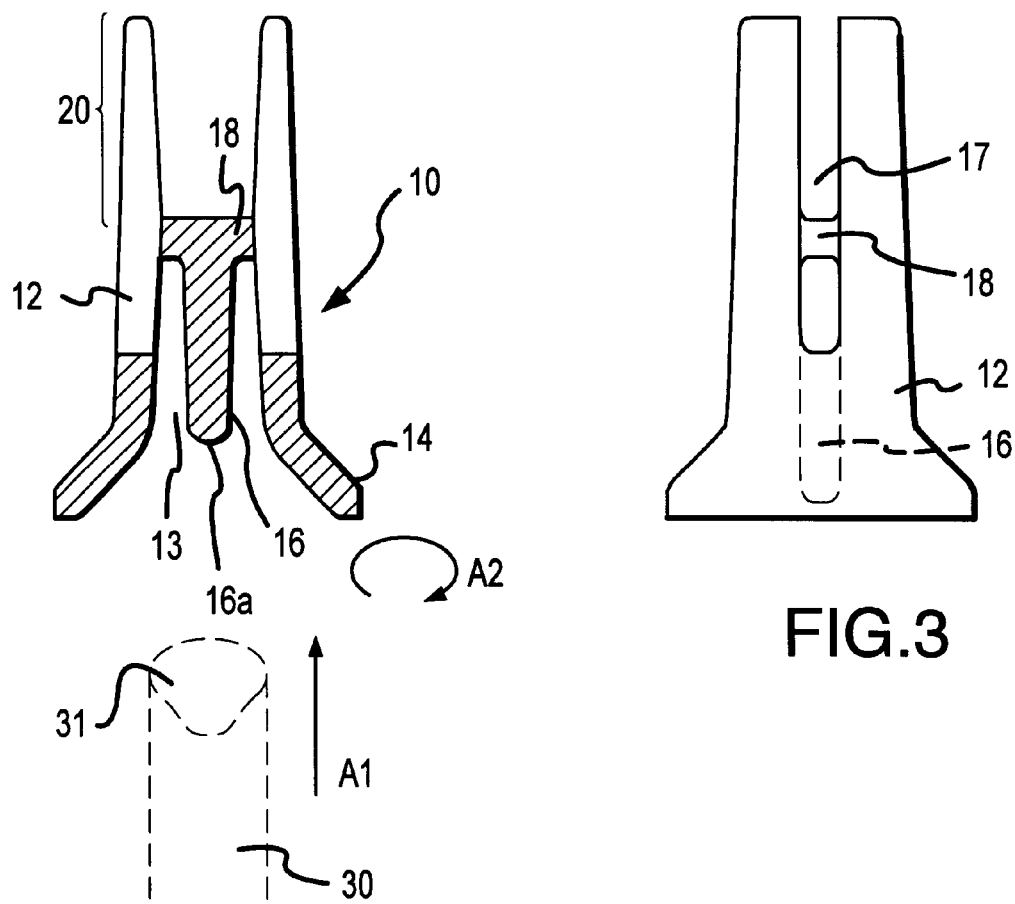
FIG.3
FIG.2

DEVICE FOR CLEANING NASAL COAGULATOR

FIELD OF THE INVENTION

The present invention relates to field of medical instruments. More particularly, the invention relates to a cleaning device adapted for cleaning a nasal coagulator or the like.

BACKGROUND

Nasal coagulators are used to achieve hemostasis in the nose. In general, such devices are relatively simple, having a tube which conducts electricity which, when applied to the interior of the nose, coagulates the blood. A more refined nasal coagulator of such type is described in U.S. patent application Ser. No. 09/877,436, the contents of which are incorporated by reference. The present invention is well suited for use with such a coagulator, and is also well suited to any similar coagulator that has a hollow conductive tube, whether intended for intra-nasal use or otherwise.

A common characteristic of such coagulators is that the coagulation process generates char which fouls the coagulator tube and which must be cleaned. Generally, the coagulator must be cleaned at least several times per operation, commonly five to ten times per operation.

The known method of cleaning a nasal coagulator is to insert a stylet into the tube and manipulate the stylet so that the char can be displaced from the tube. However, the effect may be to simply push the char deeper into the tube, which can interfere with proper operation. Also, it is somewhat difficult to operate the stylet, and the cleaning results may vary with the skill of the operator. While the stylet cleaning method is at least minimally satisfactory, as evidenced by its wide use, it will be appreciated that a cleaning device which is easier and more effective to use than known devices is a significant advance in the art. It is a primary objective of the present invention to provide such a cleaning device, which is also simple and inexpensive.

BRIEF DESCRIPTION OF THE DRAWINGS

FIG. 1 is a perspective view of a device according to an embodiment of the present invention.

FIG. 2 is a sectional elevation view of a device according to an embodiment of the present invention.

FIG. 3 is an elevation view according to an embodiment of the present invention.

REFERENCE CHARACTERS 10 cleaning device
12 cylindrical sidewall
13 interior chamber
14 flared section
16 prong
16a prong tip
17 apertures
18 web
20 lower sidewall section
30 coagulator
31 bore

DETAILED DESCRIPTION

The present invention is a device for cleaning a nasal coagulator, and a method of using the same. The device may also have utility for cleaning similar non-nasal coagulators that have a coagulating tube which accumulates char or other substance that requires cleaning.

A cleaning device 10 is displayed in overview in FIG. 1. The device 10 has a generally cylindrical sidewall 12 that partially defines a hollow interior chamber 13. The generally cylindrical sidewall 12 flares outward at a flared section 14. The flared outward section 14 preferably forms about a forty-five degree angle with respect to the sidewall 12, although the angle is not critical.

A web 18 spans the sidewall portion 12 and defines a base of the chamber 13. The web 18 forms a base, and may be referred to as such below. While the web 18 is a solid component in a preferred embodiment, the web could be non-solid. In a preferred embodiment, as shown in the drawings, the sidewall 12 extends a distance beyond the web, referred to as a lower sidewall section 20. ("Lower" is used only for convenience of reference and does not connote any other significance.) As explained below, the lower sidewall section 20 is not an essential component of the invention.

A prong 16 extends through the chamber 13 from the web 18 toward the flared section 14, terminating at a tip section 16a. The prong 16 preferably is generally cylindrical, and slightly tapers down from the web 18 to the tip section 16a. By a "slight" taper, the amount of taper as shown in FIG. 2 is a preferred amount, although it is noted that more or less taper, or even none at all, may be acceptable. The tip section 16a is preferably rounded. Preferably, the prong 16 is substantially rigid, as explained below. The tip 16 could be longer or shorter than shown.

The sidewall 12 has two apertures 17, one of which is shown in FIG. 1 and the side elevation view of FIG. 3, the other of which is preferably positioned 180 degrees around the sidewall 12. The apertures 17 preferably have a width approximately equal to the width of the prong 16. The apertures 17 extend from a position corresponding to the chamber 13 to a lower position. In a preferred embodiment, the apertures 17 continue along the entirety of the lower sidewall section 20. The extension of the aperture below the web 18 is not significant to the operation of the device, but is instead a manufacturing convenience. The operationally significant aspect of the apertures 17 is that they provide clearance from the chamber 13 to the exterior of the device 10. Neither the uppermost nor lowermost extension of the apertures 17 is critical. In a preferred embodiment, the apertures extend to a position approximately coplanar with a position midway between the web 18 and the uppermost flared portion 14. While two apertures 17 have been described, it should be appreciated that either fewer of more could be provided. Similarly, while the position of the two apertures 17 has been described as 180 degrees apart, other positions may also provide satisfactory results.

The operation of the device 10 to clean a nasal coagulator 30 is now described. The nasal coagulator 30 may be any coagulator as is known in the art of the type having a generally cylindrical exterior defining a bore 31. The coagulator 30 is positioned proximate the cleaning device 10. The coagulator 30 is advanced toward the flared section 14 of the cleaning device 10 as shown by arrow A1, so that the coagulator bore 30 is aligned with the prong 16. The advancement is continued, until the bore 30 is inserted at least partially onto the prong 16. The prong 16 dislodges accumulated char or other obstructions which may be present in the bore 31, thereby cleaning the coagulator 30. Preferably, the prong 16 is relatively rigid so that it does not flex appreciably during the cleaning operation. The coagulator 30 is then rotated in the direction shown by arrow A2 (the coagulator could be rotated in a rotational direction opposite the arrow A2 instead of or in addition to rotation in the direction of the arrow A2). This rotation is significant, as it facilitates removal of the char through the apertures 17 of the device 10. The apertures 17 thus provide a path for char and the like to exit the coagulator 30 and the cleaning device 10, and rotating the coagulator 30 improves the removal of char. Relative rotation is all that is required between the cleaning device 10 and the coagulator 20, so that either could be held stationary while the other is rotated, or both could be rotated.

The cleaning operation can be performed quickly, and requires no special skill on the part of the operator. The flared portion 14 facilities the insertion of the coagulator 30 into the chamber 13 and onto the prong 16. The apertures 17 facilitate removal of the char from the cleaning device 10. The ease of cleaning provides significant advantages to the user, particularly in light of the frequent cleaning that is required during a procedure.

It should be apparent that the invention as described in the above embodiment includes several features that are not strictly necessary. For example, the elements below the web 18 are not directly operative in the cleaning of a coagulator. However, the lower section 20 does form a useful section for an operator to grasp the device 10. As another related example, it will be noted that the sections of the aperture 17 that extend below the web 18 are not directly operative in the cleaning process. However, the manufacture of the apertures 17 may be simplified by such arrangement.

The material of the present invention is not critical to its practice. While many materials could be used, nylon is used in a preferred embodiment.

It can thus be appreciated that the present invention provides a simple, economical, and effective device to clean a nasal coagulator or the like. No particular component should be considered essential to the practice of the invention unless that is explicitly stated, as a number of features are described that may be useful alone or in combination. The scope of the invention is limited only by the claims and their legal equivalents.

What is claimed is:

1. A coagulator and a corresponding cleaning device, comprising in combination:
    a coagulator of the type having a tube defining a bore;
    a cleaning device comprising:
        (a) a cylindrical sidewall defining chamber therewithin;
        (b) a web spanning a portion of said sidewall to define a base of said chamber;
        (c) a prong positioned within said chamber, so that the coagulator bore may fitted onto the prong whereby the coagulator bore is cleaned by the prong contacting char or other obstructions contained within coagulator bore.

2. The cleaning device of claim 1, further wherein the cylindrical sidewall flares outward at a flared section.

3. The cleaning device of claim 1, wherein the flare section flares outward at an angle of approximately forty-five degrees.

4. The cleaning device of claim 1, further comprising at least one aperture in said sidewall allowing said chamber to communicate with a space exterior to said cleaning device.

5. The cleaning device of claim 4, comprising two of said at least one apertures.

6. The cleaning device of claim 5, wherein the apertures are positioned about 180 degrees apart from each other.

7. The cleaning device of claim 5, wherein the apertures are slits.

8. The cleaning device of claim 1, wherein a lower sidewall section extends below said web.

9. The cleaning device of claim 8, wherein the prong is tapered.

10. The cleaning device of claim 1, wherein the cylindrical sidewall flares outward at a flared section, and further comprising at least one aperture in said sidewall.

11. The cleaning device of claim 10, further comprising a lower sidewall section extending below said web.

12. The cleaning device of claim 11, wherein said at least one aperture comprises two slits positioned 180 degrees apart from one another.

13. The cleaning device of claim 12, wherein the prong tapers down to a rounded tip.

14. A method of cleaning a coagulator of the type having a tube defining a bore, comprising the steps of:
    inserting the coagulator bore into a cleaning device, the cleaning device having a sidewall defining a chamber, and a prong at least partially into the chamber;
    the insertion step being performed so that the bore is at least partially inserted onto said prong whereby the bore is cleaned; and
    rotating said coagulator with respect to said cleaning device.

15. The method of claim 14, wherein said chamber has at least one aperture.

16. A device for cleaning a coagulator of the type having a tube defining a bore, the device comprising:
    a cylindrical sidewall defining chamber therewithin;
    a web spanning a portion of said sidewall to define a base of said chamber;
    a prong positioned within said chamber, so that the coagulator bore may fitted onto the prong whereby the coagulator bore is cleaned;
    the sidewall having an aperture allowing communication between the chamber and a space exterior the chamber via a straight line segment.

* * * * *